US008876862B2

(12) United States Patent
Phillips (10) Patent No.: US 8,876,862 B2
(45) Date of Patent: Nov. 4, 2014

(54) HEMOSTATIC DEVICE AND ITS METHODS OF USE (75) Inventor: Victor Matthew Phillips, Jefferson City, MO (US)

(73) Assignee: Phillips Medical LLC, Jefferson City, MO (US)

(*) Notice: Subject to any disclaimer, the term of this patent is extended or adjusted under 35 U.S.C. 154(b) by 595 days.

(21) Appl. No.: 13/086,712

(22) Filed: Apr. 14, 2011

(65) Prior Publication Data

US 2012/0265243 A1    Oct. 18, 2012

(51) Int. Cl.
    *A61B 17/00* (2006.01)
(52) U.S. Cl.
    USPC ........................................... 606/213; 606/214
(58) Field of Classification Search
    USPC ............... 606/213, 214; 604/15, 264, 537; 424/426
    See application file for complete search history.

(56) References Cited

U.S. PATENT DOCUMENTS

| | | | |
|---|---|---|---|
| 4,738,658 A | 4/1988 | Magro et al. | |
| 4,850,960 A | 7/1989 | Grayzel | |
| 4,890,612 A | 1/1990 | Kensey | |
| 4,895,564 A | 1/1990 | Farrell | |
| 4,929,246 A | 5/1990 | Sinofsky | |
| 5,061,274 A | 10/1991 | Kensey | |
| 5,108,421 A | 4/1992 | Fowler | |
| 5,222,974 A | 6/1993 | Kensey et al. | |
| 5,282,827 A | 2/1994 | Kensey et al. | |
| 5,290,310 A | 3/1994 | Makower et al. | |
| 5,306,254 A | 4/1994 | Nash et al. | |
| 5,326,350 A | 7/1994 | Li | |
| RE34,866 E | 2/1995 | Kensey et al. | |
| 5,391,183 A | 2/1995 | Janzen et al. | |
| 5,415,657 A | 5/1995 | Taymor-Luria | |
| 5,431,639 A * | 7/1995 | Shaw | 604/264 |
| 5,437,292 A | 8/1995 | Kipshidze et al. | |
| 5,437,631 A | 8/1995 | Janzen | |
| 5,441,517 A | 8/1995 | Kensey et al. | |
| 5,443,481 A | 8/1995 | Lee | |
| 5,591,204 A | 1/1997 | Janzen et al. | |
| 5,645,566 A | 7/1997 | Brenneman et al. | |
| 5,653,730 A | 8/1997 | Hammerslag | |
| 5,665,107 A | 9/1997 | Hammerslag | |
| 5,676,689 A | 10/1997 | Kensey et al. | |
| 5,707,393 A | 1/1998 | Kensey et al. | |
| 5,716,375 A | 2/1998 | Fowler | |
| 5,725,498 A | 3/1998 | Janzen et al. | |
| 5,741,223 A | 4/1998 | Janzen et al. | |
| 5,766,157 A | 6/1998 | Tilton, Jr. | |
| 5,766,206 A | 6/1998 | Wijkamp et al. | |

(Continued)

OTHER PUBLICATIONS

International Search Report and Written Opinion of PCT/US2011/032490; Jun. 29, 2011; 10 pages.

*Primary Examiner* — Vy Q Bui (74) *Attorney, Agent, or Firm* — Armstrong Teasdale LLP (57) ABSTRACT

A hemostatic device is provided for sealing a puncture of a vessel. The hemostatic device includes a locator device and an injection tube coupled to the locator device. The locator device includes a device valve that is actuatable to selectively restrict access to a portion of the locator device. The hemostatic device is advanced into the vessel until a first fluid is channeled through the locator device. The device valve is actuated to selectively restrict the first fluid from being channeled through the locator device. A second fluid is injected through the injection tube to facilitate sealing a puncture of the vessel. The hemostatic device is withdrawn from the vessel.

20 Claims, 9 Drawing Sheets

(56) References Cited

U.S. PATENT DOCUMENTS

| | | |
|---|---|---|
| 5,782,861 A | 7/1998 | Cragg et al. |
| 5,843,124 A | 12/1998 | Hammerslag |
| 5,868,762 A | 2/1999 | Cragg et al. |
| 5,935,147 A | 8/1999 | Kensey et al. |
| 5,951,583 A | 9/1999 | Jensen et al. |
| 5,984,950 A | 11/1999 | Cragg et al. |
| 6,045,570 A | 4/2000 | Epstein et al. |
| 6,056,768 A | 5/2000 | Cates et al. |
| 6,090,130 A | 7/2000 | Nash et al. |
| 6,296,657 B1 | 10/2001 | Brucker |
| 6,302,898 B1 | 10/2001 | Edwards et al. |
| 6,315,753 B1 | 11/2001 | Cragg et al. |
| 6,325,789 B1 | 12/2001 | Janzen et al. |
| 6,371,974 B1 | 4/2002 | Brenneman et al. |
| 6,371,975 B2 | 4/2002 | Cruise et al. |
| 6,527,734 B2 | 3/2003 | Cragg et al. |
| 6,544,236 B1 | 4/2003 | Cragg et al. |
| 6,547,806 B1 | 4/2003 | Ding |
| 6,610,026 B2 | 8/2003 | Cragg et al. |
| 6,743,248 B2 | 6/2004 | Edwards et al. |
| 6,830,756 B2 | 12/2004 | Hnojewyj |
| 6,863,680 B2 | 3/2005 | Ashby |
| 6,984,219 B2 * | 1/2006 | Ashby et al. .............. 604/15 |
| 7,029,489 B1 | 4/2006 | Ashby et al. |
| 7,037,322 B1 * | 5/2006 | Sing et al. .............. 606/213 |
| 7,048,710 B1 | 5/2006 | Cragg et al. |
| 7,201,725 B1 | 4/2007 | Cragg et al. |
| 7,318,933 B2 | 1/2008 | Hnojewyj |
| 7,335,219 B1 | 2/2008 | Ashby et al. |
| 7,455,680 B1 | 11/2008 | Ashby et al. |
| 7,611,479 B2 | 11/2009 | Cragg et al. |
| 7,625,352 B1 | 12/2009 | Ashby et al. |
| 2001/0018598 A1 | 8/2001 | Cruise et al. |
| 2003/0088271 A1 | 5/2003 | Cragg et al. |
| 2003/0100921 A1 | 5/2003 | Addis et al. |
| 2004/0019328 A1 | 1/2004 | Sing et al. |
| 2004/0098024 A1 | 5/2004 | Dieck et al. |
| 2004/0102730 A1 | 5/2004 | Davis et al. |
| 2006/0100664 A1 | 5/2006 | Pai et al. |
| 2007/0038245 A1 | 2/2007 | Morris et al. |
| 2007/0123816 A1 | 5/2007 | Zhu et al. |
| 2008/0038313 A1 | 2/2008 | Addis et al. |
| 2008/0046005 A1 | 2/2008 | Lenker et al. |
| 2008/0071310 A1 | 3/2008 | Hoffman et al. |
| 2008/0082122 A1 | 4/2008 | Khosravi et al. |
| 2008/0161849 A1 | 7/2008 | Cates et al. |
| 2009/0088793 A1 | 4/2009 | Bagaoisan et al. |
| 2009/0143808 A1 | 6/2009 | Houser |
| 2009/0171282 A1 | 7/2009 | Pipenhagen et al. |

* cited by examiner

HEMOSTATIC DEVICE AND ITS METHODS OF USE

CROSS REFERENCE TO RELATED APPLICATIONS

This application claims the benefit of U.S. application Ser. No. 12/762,886, filed Apr. 19, 2010, which claims priority to U.S. Provisional Application No. 61/267,685, filed Dec. 8, 2009. Each patent application is incorporated herein by reference in its entirety.

BACKGROUND OF THE INVENTION

The subject matter described herein relates generally to medical devices and, more particularly, to a hemostatic device.

Catheter introducers are known to provide an access site to an artery for at least some medical procedures such as cardiac catheterizations or peripheral endovascular procedures. After such medical procedures are conducted, the catheter introducer is removed from the access site, leaving an arterial opening. Generally, excess blood loss endangers and/or traumatizes the patient. One known method of controlling blood loss is through direct manual pressure over the access site.

BRIEF SUMMARY OF THE INVENTION

In one aspect, a method is provided for sealing a puncture of a vessel. The method includes advancing a hemostatic device into the vessel until a first fluid is channeled through a locator device. A device valve is actuated to selectively restrict the first fluid from being channeled through the locator device. A second fluid is injected through an injection tube to facilitate sealing a puncture of the vessel. The hemostatic device is withdrawn from the vessel.

In another aspect, a hemostatic device is provided for sealing a puncture of a vessel. The hemostatic device includes a locator device and an injection tube coupled to the locator device. The locator device includes a device valve that is actuatable to selectively restrict access to a portion of the locator device. The locator device is configured to channel a first fluid therethrough. The injection tube is configured to channel a second fluid therethrough.

In yet another aspect, a hemostatic device is provided for sealing a puncture of a vessel. The hemostatic device includes a locator device and an injection tube coupled to the locator device. The locator device includes a device sidewall and a device valve. The device sidewall defines a device lumen that is configured to channel a first fluid therethrough. The device valve is actuatable to selectively restrict access to the device lumen. The injection tube includes a tube sidewall that defines a tube lumen configured to channel a second fluid therethrough.

DETAILED DESCRIPTION OF THE INVENTION

The methods and apparatus described herein relate to medical devices and, more particularly, to a hemostatic device. The hemostatic device described herein facilitates sealing a puncture of a vessel. More particularly, the hemostatic device enables positioning an injection tube adjacent the vessel to inject a gelatin through the injection tube. As such, the hemostatic device facilitates reducing a time required for hemostasis and ambulation.

Figure 1:
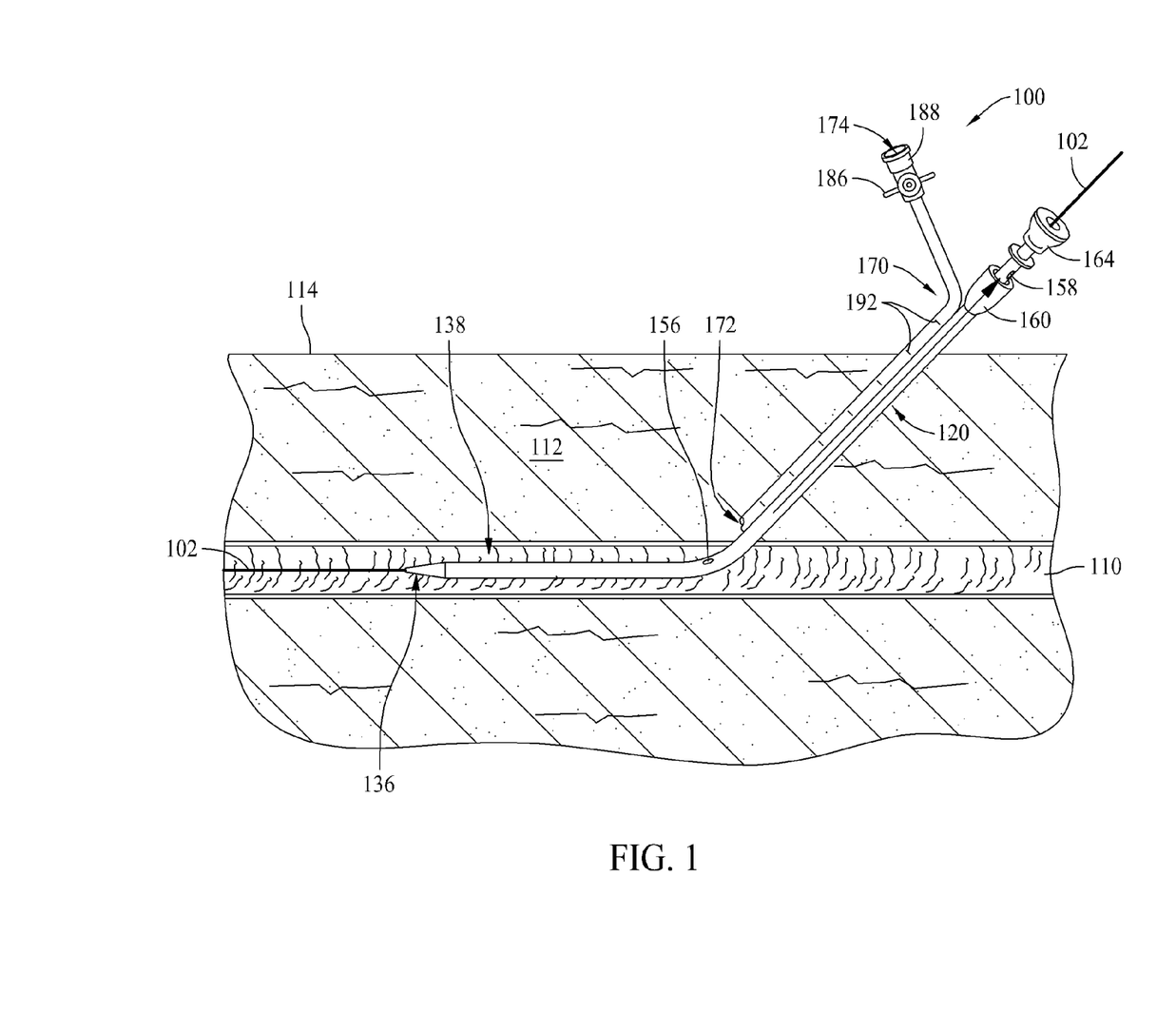
FIG. 1 is a partial cross-sectional view of an access site including an exemplary hemostatic device.
Figure 2:
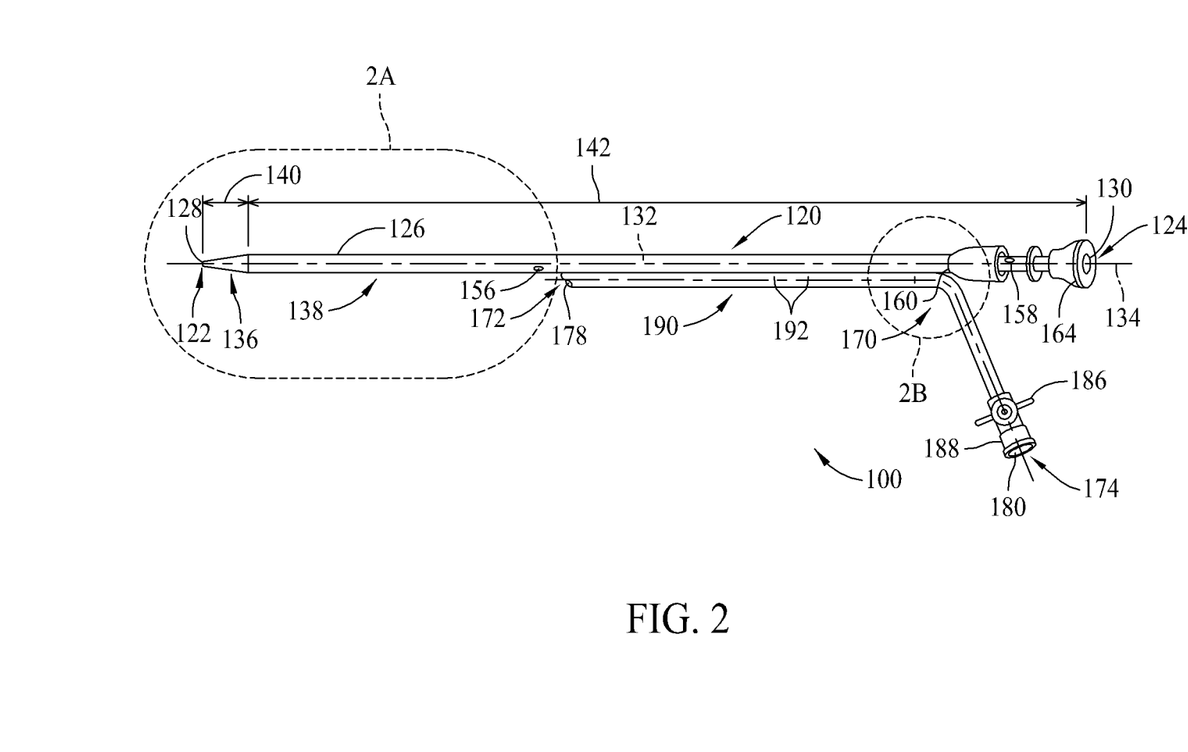
FIG. 2 is a perspective view of the hemostatic device shown in FIG. 1.
Figure 2A:
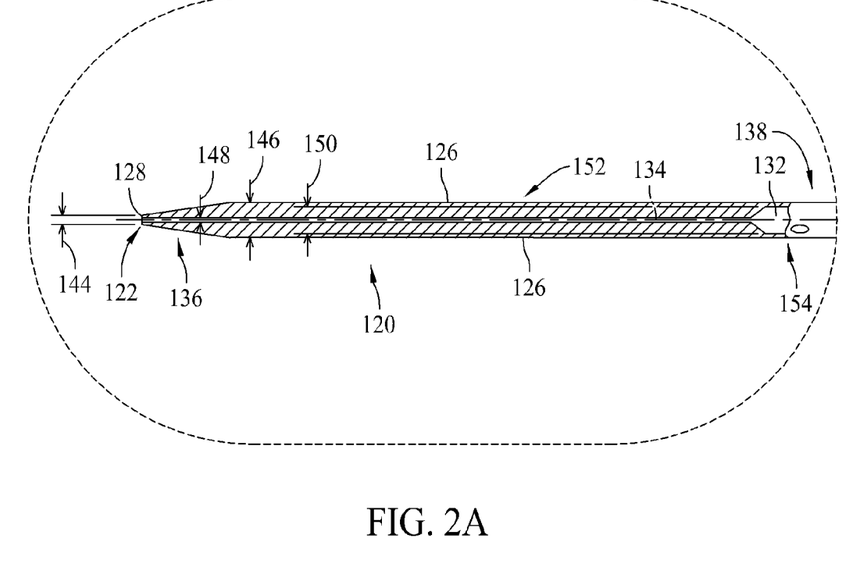
FIGS. 2A and 2B are cut-away views of the hemostatic device shown in FIG. 1.
Figure 2B:
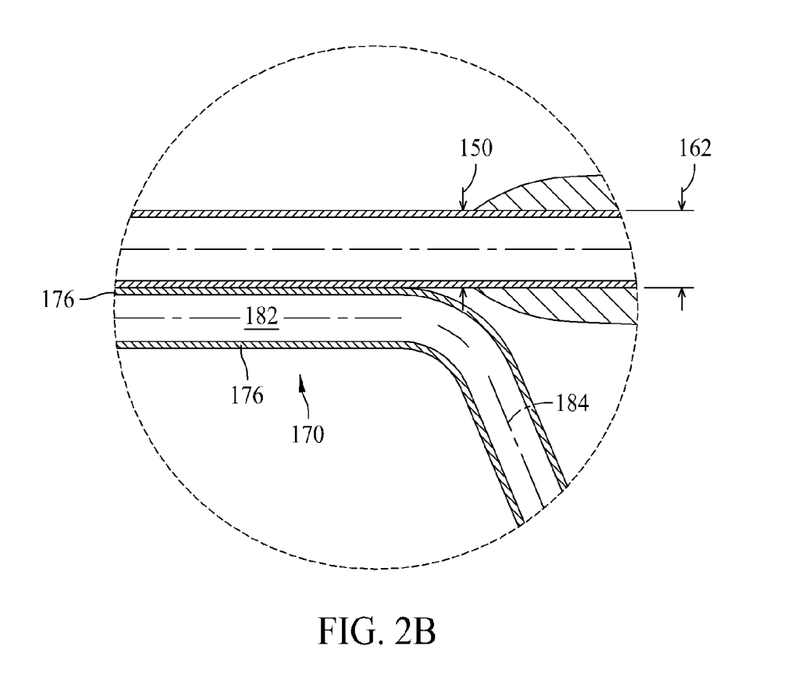

FIG. 1 is a partial cross-sectional view of an access site including an exemplary hemostatic device 100, a guidewire 102, and a vessel or, more particularly, an artery 110 within subcutaneous tissue 112 under a skin surface 114. FIG. 2 is a perspective view of hemostatic device 100, and FIGS. 2A and 2B are detailed cut-away views of hemostatic device 100. In the exemplary embodiment, hemostatic device 100 includes a locator device 120 having a distal end 122 and a proximal end 124. In the exemplary embodiment, locator device 120 extends longitudinally approximately 20.0 centimeters (cm) from distal end 122 to proximal end 124.

In the exemplary embodiment, locator device 120 includes a sidewall 126 having a distal end opening 128, a proximal end opening 130, and a lumen 132 defined therebetween substantially aligned along a center axis 134. In the exemplary embodiment, lumen 132 is configured to channel a first fluid therethrough.

In the exemplary embodiment, locator device 120 includes a first section 136 and a second section 138. First section 136 extends longitudinally a first distance 140 from distal end 122, and second section 138 extends longitudinally a second distance 142 from proximal end 124. First distance 140 is at least approximately 0.5 cm, and second distance 142 is at most approximately 19.5 cm. More particularly, in the exemplary embodiment, first distance 140 is approximately 1.0 cm, and second distance 142 is approximately 19.0 cm.

In the exemplary embodiment, locator device 120 is tapered at distal end 122 to facilitate traversing locator device 120 under skin surface 114 and through subcutaneous tissue 112. First section 136 has a first outer diameter 144, and second section 138 has a second outer diameter 146 that is larger than first outer diameter 144. Second outer diameter 146 is approximately 2 millimeters (mm) or 6 French (Fr). In another embodiment, second outer diameter 146 is approximately 2.67 mm or 8 Fr. In yet another embodiment, second outer diameter 146 is approximately 3.33 mm or 10 Fr.

In the exemplary embodiment, locator device 120 is configured to receive guidewire 102 that extends longitudinally therethrough. More specifically, distal end opening 128, first section 136, second section 138, and proximal end opening 130 are sized such that guidewire 102 is capable of extending longitudinally through lumen 132 between proximal end opening 130 and distal end opening 128. In the exemplary embodiment, guidewire 102 has an outer diameter of approximately 0.035 inches or 0.089 cm.

In the exemplary embodiment, first section 136 has a first inner diameter 148 that is approximately 0.089 cm, and second section 138 has a second inner diameter 150 that is larger than approximately 0.089 cm. More specifically, in the exemplary embodiment, second section 138 has a first subsection 152 that has first inner diameter 148 and a second subsection 154 that has second inner diameter 150. In one embodiment, second inner diameter 150 is approximately 0.059 inches or 0.150 cm. In another embodiment, second inner diameter 150 is approximately 0.087 inches or 0.221 cm. In yet another embodiment, second inner diameter 150 is approximately 0.113 inches or 0.287 cm.

As shown in FIG. 1, sidewall 126 includes a distal opening 156 and a proximal opening 158 extending radially therethrough. Distal opening 156 and proximal opening 158 are in fluid communication with lumen 132. In the exemplary embodiment, distal opening 156 and proximal opening 158 are positioned within second section 138. More specifically, in the exemplary embodiment, first subsection 152 extends longitudinally between first section 136 and distal opening 156, and second subsection extends longitudinally between distal opening 156 and proximal end 124. In the exemplary embodiment, distal opening 156 is positioned approximately 8.0 cm from distal end 122, and proximal opening 158 is positioned approximately 1.0 cm from proximal end 124.

In the exemplary embodiment, locator device 120 includes a first device valve 160 positioned adjacent proximal opening 158. First device valve 160 is actuatable between an open position and a closed position to selectively restrict access to a portion of locator device 120. In the open position, proximal opening 158 is at least partially exposed such that the fluid may flow into and/or out from lumen 132 through proximal opening 158. In contrast, in the closed position, proximal opening 158 is substantially covered by first device valve 160 such that a fluid is restricted from flowing into and/or out from lumen 132 through proximal opening 158. In the exemplary embodiment, first device valve 160 is a sleeve that has an inner diameter 162 that is larger than second outer diameter 146 such that first device valve 160 is slidable about second section 138. In the exemplary embodiment, first device valve 160 extends longitudinally approximately 1.0 cm about locator device 120.

Additionally, in the exemplary embodiment, locator device 120 includes a second device valve 164 positioned adjacent proximal end opening 130. Second device valve 164 is actuatable between an open position and a closed position to selectively restrict access to a portion of locator device 120. In the open position, proximal end opening 130 is at least partially exposed such that guidewire 102 may extend through proximal end opening 130. In contrast, in the closed position, proximal end opening 130 is substantially covered by second device valve 164 such that a fluid is restricted from flowing into and/or out from lumen 132 through proximal end opening 130. In the exemplary embodiment, second device valve 164 is a manual-adjusting valve.

In the exemplary embodiment, hemostatic device 100 further includes an injection tube 170 having a distal end 172 and a proximal end 174. Injection tube 170 extends longitudinally at least approximately 6.0 cm from distal end 172 to proximal end 174. More particularly, injection tube 170 extends longitudinally approximately 8.0 cm from distal end 172 to proximal end 174. Injection tube 170 includes a sidewall 176 having a distal end opening 178, a proximal end opening 180, and a lumen 182 defined therebetween. In the exemplary embodiment, distal end opening 178, proximal end opening 180, and lumen 182 are substantially aligned along a center axis 184, and lumen 182 is configured to channel a second fluid therethrough.

In the exemplary embodiment, injection tube 170 is coupled to locator device 120 such that distal end 172 of injection tube 170 is positionable substantially adjacent artery 110. More specifically, when distal opening 156 of locator device 120 is positioned within artery 110, distal end 172 is positionable substantially adjacent, and outside, artery 110. Distal end 172 of injection tube 170 is positioned approximately 9.0 cm from distal end 122 of locator device 120 such that distal end 172 is positioned approximately 1.0 cm from distal opening 156. In one embodiment, locator device 120 and injection tube 170 are substantially concentric.

In the exemplary embodiment, injection tube 170 includes a tube valve 186 positioned adjacent proximal end opening 180. Tube valve 186 is actuatable between an open position and a closed position to selectively restrict access to a portion of tube valve 186. In the open position, proximal end opening 180 is at least partially exposed such that the fluid may flow into and/or out from lumen 182 through proximal end opening. In contrast, in the closed position, proximal end opening 180 is substantially covered by tube valve 186 such that a fluid is restricted from flowing into and/or out from lumen 182 through proximal end opening 180. In the exemplary embodiment, tube valve 186 is a stop cock and includes a side port 188. In the exemplary embodiment, the fluid may be injected into lumen 182 through side port 188.

Injection tube 170 includes an indicator 190 that indicates a length of locator device 120 and/or injection tube 170. More specifically, indicator 190 provides an indication of how much of injection tube 170 is under skin surface 114. In the exemplary embodiment, indicator 190 includes a plurality of markings 192 that are spaced evenly along injection tube 170. More specifically, in the exemplary embodiment, there is at least one marking 192 for each centimeter of injection tube 170.

Figure 3:
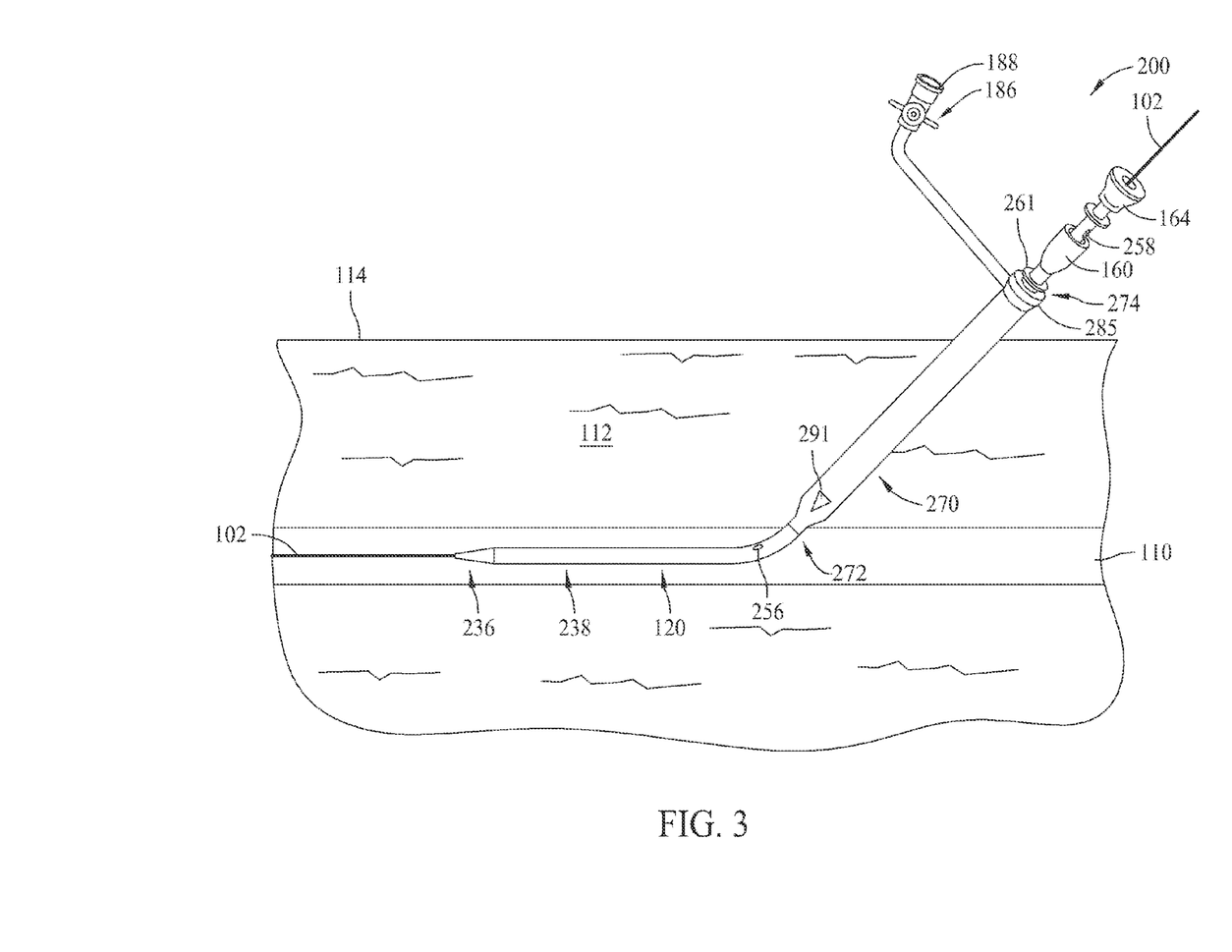
FIG. 3 is a partial cross-sectional view of an access site including an alternative hemostatic device.
Figure 4:
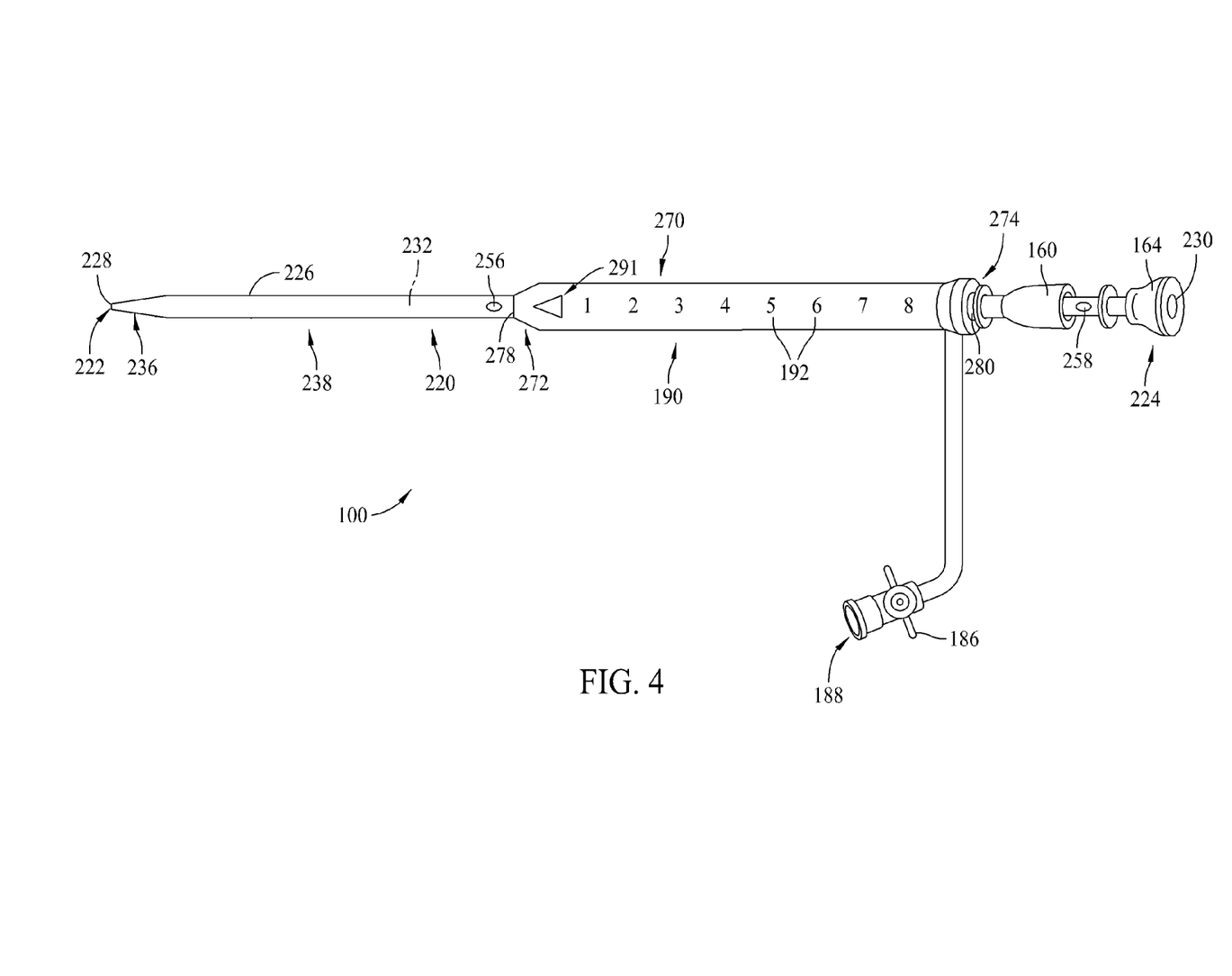
FIG. 4 is a perspective view of the hemostatic device shown in FIG. 3.

FIG. 3 is a partial cross-sectional view of the access site including an alternative hemostatic device 200. FIG. 4 is a perspective view of hemostatic device 200. In the exemplary embodiment, hemostatic device 200 includes a locator device 220, also shown in FIG. 5, that is substantially similar to locator device 120 described in more detail above. In the exemplary embodiment, locator device 220 includes a distal end 222 and a proximal end 224. Distal end 222 is tapered to facilitate traversing locator device 220 under skin surface 114 and through subcutaneous tissue 112.

Figure 5:
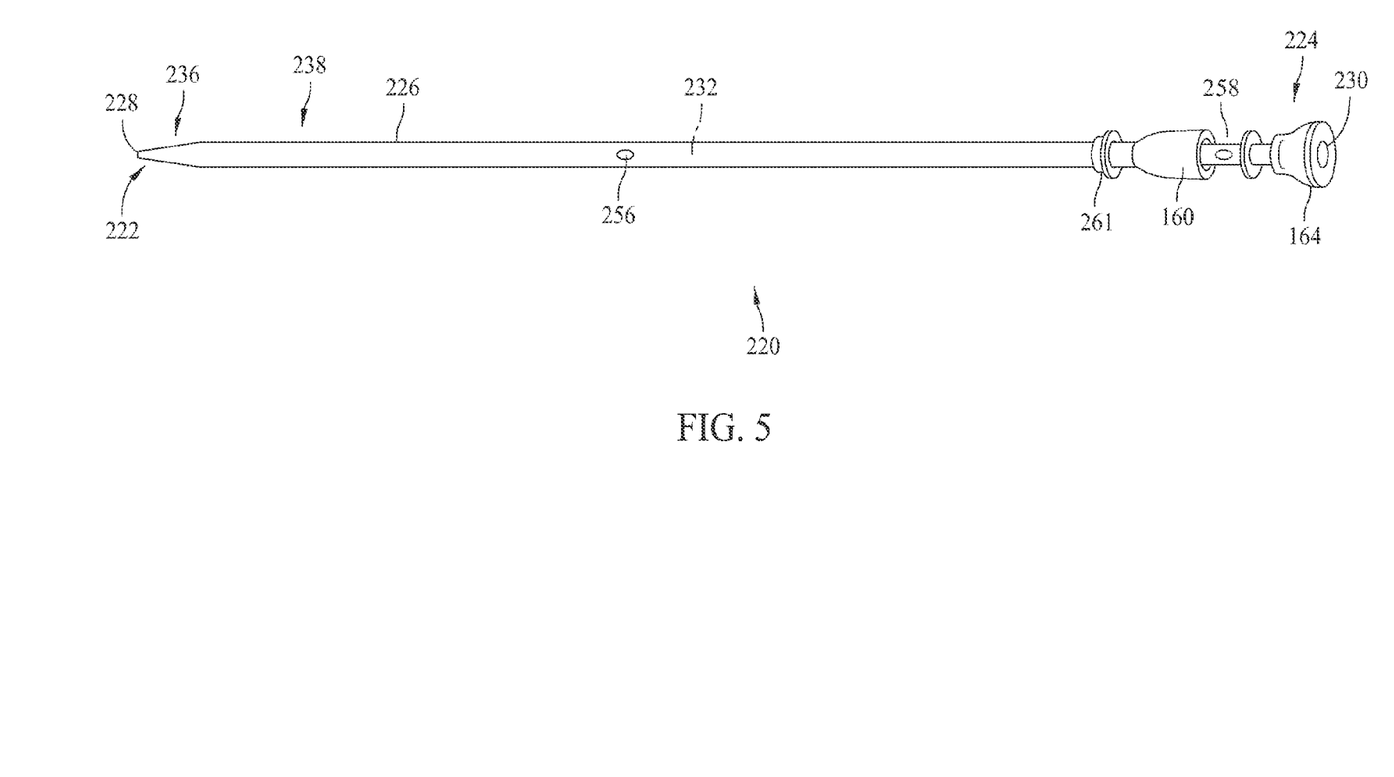
FIG. 5 is a perspective view of a locator device that may be used with the hemostatic device shown in FIG. 3.
Figure 6:
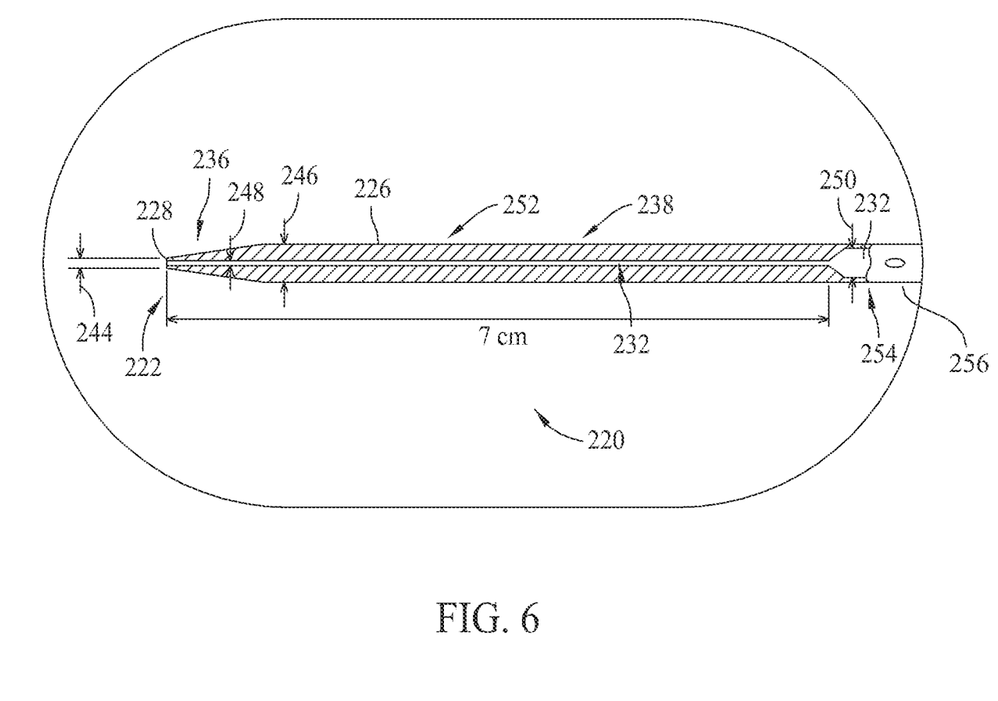
FIG. 6 is a cut-away view of the locator device shown in FIG. 5.

In the exemplary embodiment, locator device 220 includes a sidewall 226 having a distal end opening 228, a proximal end opening 230, and a lumen 232 defined therebetween sized to channel the first fluid therethrough. More specifically, as shown in FIG. 6, locator device 220 includes first section 236 having a first outer diameter 244, and a second section 238 having a second outer diameter 246 that is larger than first outer diameter 244. In one embodiment, second outer diameter 246 is approximately 0.099 inches or 0.251 cm for the 6 Fr system. In another embodiment, second outer diameter 246 is approximately 0.125 inches or 0.318 cm for the 8 Fr system. Alternatively, second outer diameter 246 may be any suitable width that enables locator device 220 to function as described herein.

Moreover, as shown in FIG. 6, first section 236 has a first inner diameter 248 that is approximately 0.889 mm, and second section 238 has a second inner diameter 250 that is sized to enable an inner flow lumen to be defined around guidewire 102. More specifically, in the exemplary embodiment, second section 238 has a first subsection 252 that has first inner diameter 248 and a second subsection 254 that has second inner diameter 250 that is larger than first inner diameter 248. In the exemplary embodiment, first subsection 252 extends longitudinally approximately 7.0 cm from distal end 222. In one embodiment, second inner diameter 250 is approximately 0.081 inches or 0.206 cm for the 6 Fr system. In another embodiment, second inner diameter 250 is approximately 0.107 inches or 0.272 cm for the 8 Fr system. Alternatively, second inner diameter 250 may be any suitable width that enables locator device 220 to function as described herein.

In the exemplary embodiment, sidewall 226 includes a distal opening 256 and a proximal opening 258 extending radially therethrough. Distal opening 256 and proximal opening 258 are in fluid communication with lumen 232. In the exemplary embodiment, distal opening 256 and proximal opening 258 are positioned within second section 238. More specifically, in the exemplary embodiment, first subsection 252 extends longitudinally between first section 236 and distal opening 256, and second subsection extends longitudinally between distal opening 256 and proximal end 224. In the exemplary embodiment, distal opening 256 is positioned approximately 8.0 cm from distal end 222, and proximal opening 258 is positioned approximately 3.0 cm from proximal end 224. Alternatively, distal opening 256 and proximal opening 258 may be positioned at any suitable location that enables locator device 220 to function as described herein.

In the exemplary embodiment, first device valve 160 is positioned adjacent proximal opening 258. First device valve 160 is actuatable between the open position and the closed position to selectively restrict access to at least a portion of locator device 220, as described in more detail above with respect to locator device 120. Moreover, in the exemplary embodiment, second device valve 164 is positioned adjacent proximal end opening 230. Second device valve 164 is actuatable between the open position and the closed position to selectively restrict access to a portion of locator device 220, as described in more detail above with respect to locator device 120.

Figure 7:
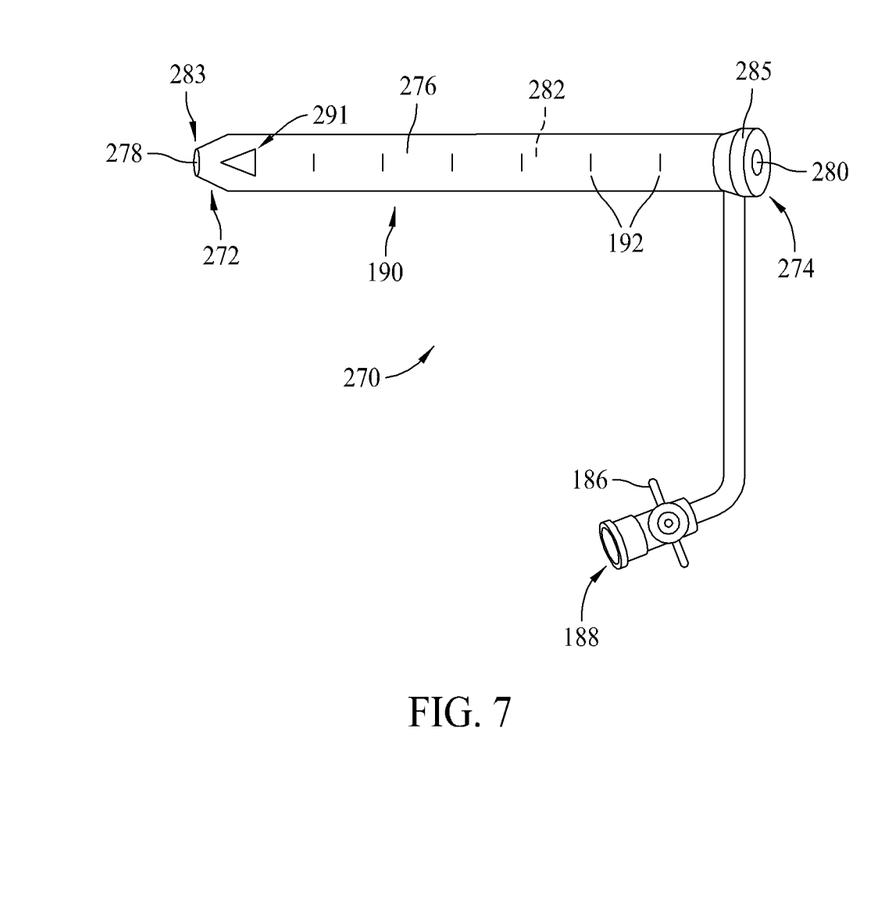
FIG. 7 is a perspective view of an injection tube that may be used with the hemostatic device shown in FIG. 3.

Locator device 220 includes a cap 261 coupleable to an injection tube 270, also shown in FIG. 7, that is substantially similar to injection tube 170. In the exemplary embodiment, injection tube 270 has a distal end 272 and a proximal end 274. Injection tube 270 is tapered at distal end 272 to facilitate traversing injection tube 270 under skin surface 114 and through subcutaneous tissue 112.

Injection tube 270 includes a sidewall 276 having a distal end opening 278, a proximal end opening 280, and a lumen 282 defined therebetween. In the exemplary embodiment, distal end opening 278 includes a distal valve 283 configured to receive locator device 220 such that locator device 220 and injection tube 270 are substantially coaxial. More specifically, in the exemplary embodiment, locator device 220 is advanceable through distal valve 283 such that injection tube 270 substantially houses at least a portion of locator device 220. In the exemplary embodiment, locator device 220 is advanced until a proximal valve 285 positioned at injection tube proximal end 274 is coupled to cap 261 such that injection tube distal end 272 may be positioned substantially adjacent distal opening 256. In the exemplary embodiment, injection tube distal end 272 is positionable approximately 9.0 cm from locator device distal end 222 and/or approximately 1.0 cm from locator device distal opening 256. As such, when locator device distal opening 256 is positioned within artery 110, injection tube distal end 272 is positioned substantially adjacent, and outside, artery 110.

In the exemplary embodiment, injection tube 270 has a first inner diameter 287 adjacent distal end 272 that is substantially similar to locator device second outer diameter 246. In one embodiment, first inner diameter 287 is approximately 0.099 inches or 0.251 cm for the 6 Fr system. In another embodiment, first inner diameter 287 is approximately 0.125 inches or 0.318 cm for the 8 Fr system. In the exemplary embodiment, injection tube 270 has a second inner diameter 289 that is sized to channel the second fluid through lumen 282 about locator device 220. As such, second inner diameter 289 is wider than first inner diameter 287 or, more specifically, locator device second outer diameter 246 in the exemplary embodiment. In one embodiment, second inner diameter 289 is approximately 0.139 inches or 0.353 cm for the 6 Fr system. In another embodiment, second inner diameter 289 is approximately 0.165 inches or 0.419 cm for the 8 Fr system.

In the exemplary embodiment, side port 188 extends from injection tube 270 and is communicatively coupled to lumen 282. Side port 188 includes tube valve 186 that is actuatable between the open position and the closed position to selectively restrict access to a portion of tube valve 186, as described in more detail above with respect to injection tube 170. The second fluid is injectable into side port 188, through lumen 282, and discharged from a plurality of side openings 291 extending through sidewall 276. Side openings 291 are spaced substantially evenly about a circumference of injection tube 270. For example, in one embodiment, side openings 289 are positioned at each quadrant of sidewall 276.

In the exemplary embodiment, side openings 291 are positioned adjacent distal opening 156. More specifically, side openings 291 are spaced between approximately 5.0 mm and 10.0 mm from a distal end of injection tube 270. As such, when distal opening 256 is positioned within artery 110, side openings 291 are positionable substantially adjacent, and outside, artery 110 to facilitate sealing the puncture of artery 110.

Figure 8:
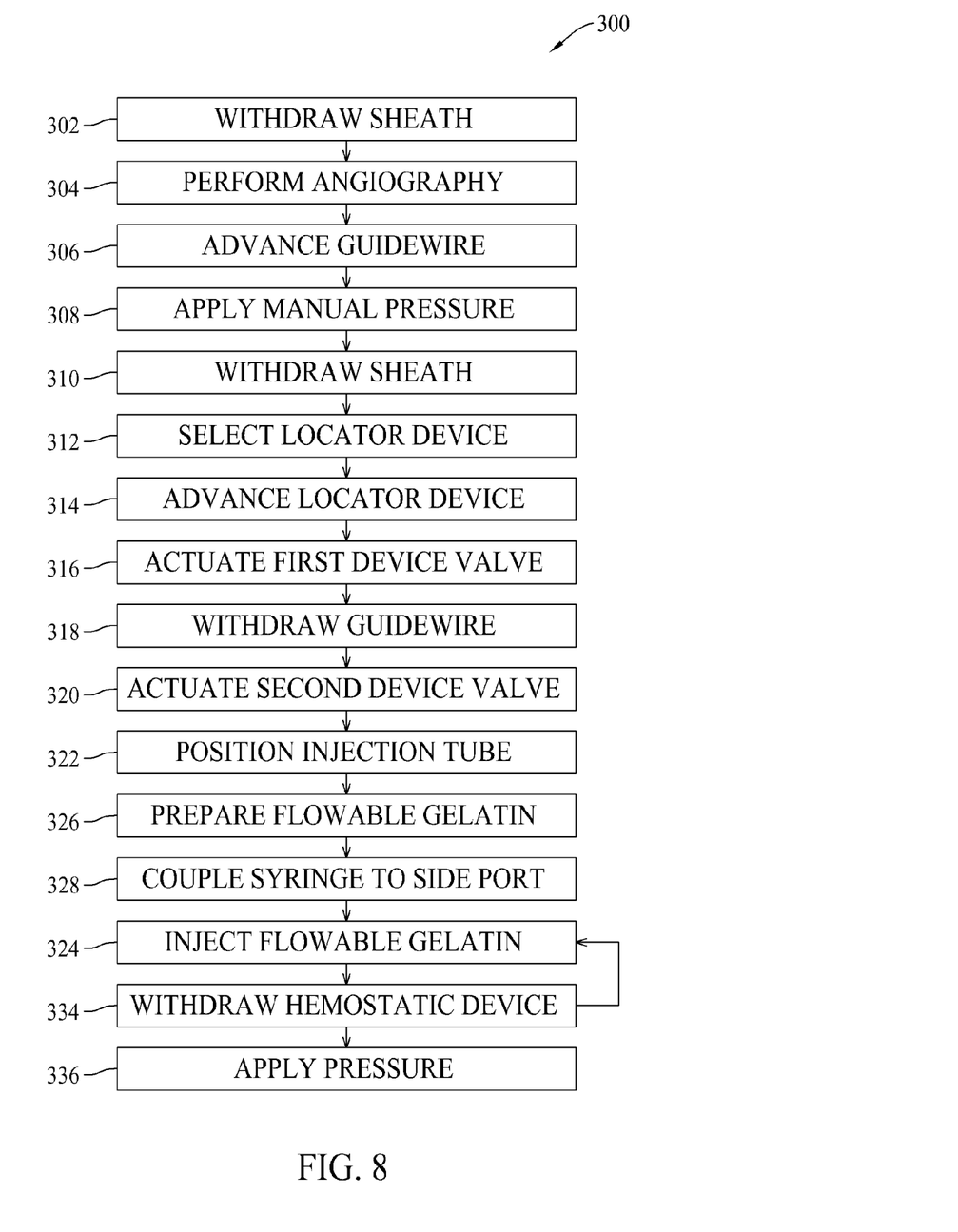
FIG. 8 is a flow chart illustrating an exemplary method using the hemostatic device shown in FIG. 1 and/or FIG. 3.

FIG. 8 is a flow chart illustrating an exemplary method 300 using hemostatic device 100 and/or 200. During operation, hemostatic device 100 and/or 200 is used for sealing a puncture of artery 110 within subcutaneous tissue 112 under a skin surface 114.

In the exemplary embodiment, a sheath (not shown) used during a medical procedure, such as a cardiac catheterization or a peripheral endovascular procedure, is withdrawn 302 such that a tip of the sheath is positioned approximately 10.0 cm from the access site and the sheath is free of at least some devices. A limited angiography is performed 304 through the sheath to assess the puncture of artery 110 and to ensure that the sheath is positioned within artery 110.

In the exemplary embodiment, guidewire 102 is advanced 306 through the sheath to artery 110 such that a tip of guidewire 102 is positioned at least approximately 5.0 cm beyond the tip of the sheath. More particularly, guidewire 102 is advanced 306 to position the tip of guidewire 102 approximately 10.0 cm beyond the tip of the sheath. Manual pressure is applied 308 over the access site, and the sheath is withdrawn 310 from the access site over guidewire 102. Locator device 120 and/or 220 is determined or selected 312 based on a size of the sheath. For example, in one embodiment, locator device 120 and/or 220 is selected 312 to have an outer diameter that is approximately the same as an outer diameter of the sheath. More specifically, in such an embodiment, the 6 Fr system may be used with, without limitation, a sheath having a diameter between approximately 4 Fr and 6 Fr, and the 8 Fr system may be used with, without limitation, a sheath having a diameter between approximately 6 Fr and 8 Fr.

In the exemplary embodiment, locator device 120 and/or 220 is advanced 314 into artery 110 until a first fluid is channeled through locator device 120 and/or 220. More specifically, in the exemplary embodiment, locator device 120 and/or 220 is advanced 314 or slid along guidewire 102 under skin surface 114, through subcutaneous tissue 112, and to artery 110 until distal opening 156 and/or 256 is positioned within artery 110 and a fluid such as blood flows into distal opening 156 and/or 256, through lumen 132 and/or 232, and out from proximal opening 158 and/or 258. In the exemplary embodiment, locator device 120 and/or 220 is advanced 314 under skin level for approximately 8.0 cm.

Proximal opening 158 and/or 258 provides a visual cue that distal opening 156 and/or 256 is within artery 110 when the blood flows through proximal opening 158 and/or 258. To reduce an amount of blood that refluxes through proximal opening 158 and/or 258, first device valve 160 is actuated 316 to the closed position to restrict the blood from flowing out from proximal opening 158 and/or 258 and/or through lumen 132 and/or 232. Moreover, guidewire 102 is withdrawn 318 from artery 110 and/or locator device 120 and/or 220, and second device valve 164 is actuated 320 to the closed position to restrict the blood from flowing through proximal end opening 130 and/or through lumen 132 and/or 232.

Injection tube distal end 172 and/or 272 is positioned 322 substantially adjacent artery 110. More specifically, the relative positioning of locator device 120 and/or 220 and injection tube 170 and/or 270 enables injection tube distal end 172 and/or 272 to be positioned 322 substantially adjacent, and just outside, artery 110 when distal opening 156 and/or 256 is initially advanced within artery 110.

In the exemplary embodiment, a second fluid or, more particularly, a flowable gelatin is injected 324 around artery 110 and along a tract through subcutaneous tissue 112 between artery 110 and skin surface 114 through injection tube 170 and/or 270 to facilitate sealing the puncture of artery 110. More specifically, in the exemplary embodiment, the flowable gelatin is prepared 326 and received within a syringe (not shown), and the syringe is coupled 328 to injection tube side port 188.

In the exemplary embodiment, the flowable gelatin discharged from side openings 291 to facilitate sealing the access site. The injection process may be repeated as hemostatic device 100 and/or 200 is withdrawn 334 from artery 110 a length at a time until hemostatic device 100 and/or 200 is substantially withdrawn from subcutaneous tissue 112. More specifically, in such an embodiment, hemostatic device 100 and/or 200 may be systematically positioned within subcutaneous tissue 112 based on at least one length indicated by indicator 190 to enable the flowable gelatin to be systematically injected 324 through injection tube 170 and/or 270 at each position. In one embodiment, indicator 190 provides a visual cue that a length of injection tube 170 and/or 270 is under skin surface 114 and facilitates maintaining the length and/or systematically adjusting the length. Additionally or alternatively, side port 188 may be rotated approximately 180° about center axis 134 to inject additional flowable gelatin through injection tube 170.

In the exemplary embodiment, when injection tube distal end 172 and/or 272 is substantially adjacent skin surface 114, hemostatic device 100 and/or 200 is withdrawn 334 from artery 110 and/or subcutaneous tissue 112. In the exemplary embodiment, direct, non-occlusive manual pressure is continuously applied 336 to the access site until hemostasis is achieved.

The methods and systems described herein relate to medical devices and, more particularly, to a hemostatic device. The hemostatic device described herein facilitates sealing a puncture of a vessel. More particularly, the hemostatic device enables positioning an injection tube adjacent the vessel to inject a gelatin through the injection tube. As such, the hemostatic device facilitates reducing a time required for hemostasis and ambulation.

Exemplary embodiments of medical devices are described above in detail. The methods and systems are not limited to the specific embodiments described herein, but rather, operations of the methods and components of the systems may be utilized independently and separately from other operations and/or components described herein. For example, the methods and apparatus described herein may have other industrial and/or consumer applications and are not limited to practice with medical devices as described herein. Rather, one or more embodiments may be implemented and utilized in connection with other industries.

As used herein, an element or step recited in the singular and proceeded with the word "a" or "an" should be understood as not excluding plural said elements or steps, unless such exclusion is explicitly stated. Further, references to "one embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for sealing a puncture of a vessel using a locator device configured to extend through a distal end of an injection tube such that the injection tube houses at least a portion of the locator device and the injection tube and the locator device are substantially coaxial, the injection tube including a sidewall that includes at least one discharge port extending therethrough proximate the distal end of the injection tube, said method comprising:
    advancing the locator device into the vessel until a first fluid is channeled through a first lumen defined by an inner surface of the locator device;
    actuating a device valve to selectively restrict the first fluid from being channeled through the first lumen;
    injecting a second fluid through a second lumen defined by an outer surface of the locator device and an inner surface of the injection tube;
    discharging the second fluid through the at least one discharge port to facilitate sealing a puncture of the vessel; and
    withdrawing the hemostatic device from the vessel.

2. A method in accordance with claim 1, wherein advancing the locator device further comprises:
    advancing a guidewire towards the vessel;
    sliding the locator device along the guidewire towards the vessel until a first opening of the locator device is positioned within the vessel such that the first fluid is channeled from the first opening to a second opening of the locator device;
    actuating a second device valve to selectively restrict the first fluid from being channeled through the first lumen; and positioning the distal end of the injection tube substantially adjacent the vessel.

3. A method in accordance with claim 1, wherein injecting a second fluid further comprises:
injecting a first portion of the second fluid through the second lumen;
withdrawing the locator device from the vessel a predetermined length indicated by an indicator; and
injecting a second portion of the second fluid through the second lumen.

4. A hemostatic device for sealing a puncture of a vessel, said hemostatic device comprising:
a locator device comprising a first sidewall and a device valve, the locator device including a first opening extending through the first sidewall and configured to channel a first fluid through the first side opening and through a first lumen defined by an inner surface of the first sidewall, the device valve actuatable to selectively restrict access to the first lumen; and
an injection tube comprising a second sidewall housing at least the portion of the locator device, the injection tube aligned substantially coaxially with the locator device, the injection tube including at least one discharge port extending through the second sidewall and configured to channel a second fluid through a second lumen defined by an outer surface of the first sidewall and an inner surface of the second sidewall and discharge the second fluid from the at least one second side opening.

5. A hemostatic device in accordance with claim 4, wherein the locator device includes a second opening extending through the first sidewall, the first opening in fluid communication with the second opening, wherein a distal end of the injection tube is positionable substantially adjacent the vessel when the first fluid is channeled from the first opening to the second opening.

6. A hemostatic device in accordance with claim 4, wherein the first sidewall includes a first section having a first inner diameter and a second section having a second inner diameter that is different from the first inner diameter, and has an outer diameter that tapers toward a distal end of the locator device.

7. A hemostatic device in accordance with claim 4, wherein the locator device further comprises a second device valve that is actuatable to selectively restrict access to the first lumen.

8. A hemostatic device in accordance with claim 4, wherein the locator device further comprises a cap coupled to a proximal end of the injection tube.

9. A hemostatic device in accordance with claim 4, wherein the second sidewall includes a first section having a first inner diameter and a second section having a second inner diameter that is different from the first inner diameter, and has an outer diameter that tapers towards a distal end of the injection tube.

10. A hemostatic device in accordance with claim 4, wherein the injection tube further comprises a tube valve that is actuatable to selectively provide access to a portion of the injection tube.

11. A hemostatic device in accordance with claim 4, wherein at least one of the locator device and the injection tube further comprises an indicator that indicates a length of at least one of the locator device and the injection tube.

12. A hemostatic device for sealing a puncture of a vessel, said hemostatic device comprising:
a locator device comprising a device sidewall and a device valve, an inner surface of the device sidewall defining a device lumen that is configured to channel a first fluid therethrough, the device valve actuatable to selectively restrict access to the device lumen; and
an injection tube housing at least a portion of the locator device, the injection tube aligned substantially coaxially with the locator device, the injection tube comprising a tube sidewall that includes at least one discharge port extending therethrough proximate a distal end of the injection tube, an outer surface of the device sidewall and an inner surface of the tube sidewall defining a tube lumen configured to channel a second fluid therethrough towards the at least one discharge port.

13. A hemostatic device in accordance with claim 12, wherein the device sidewall includes a first opening and a second opening extending therethrough, the device lumen in fluid communication with the first and second openings, and wherein the distal end of the injection tube is positionable substantially adjacent the vessel when the first opening of the locator device is positioned within the vessel.

14. A hemostatic device in accordance with claim 12, wherein the device sidewall comprises a first section having a first inner diameter and a second section having a second inner diameter that is different from the first inner diameter, the device sidewall having an outer diameter that tapers toward a distal end of the locator device.

15. A hemostatic device in accordance with claim 12, wherein the locator device further comprises a second device valve that is actuatable to selectively provide access to the device lumen.

16. A hemostatic device in accordance with claim 12, wherein the tube sidewall includes a first section having a first inner diameter and a second section having a second inner diameter that is different from the first inner diameter, the tube sidewall having an outer diameter that tapers towards the distal end of the injection tube.

17. A hemostatic device in accordance with claim 12, wherein the injection tube further comprises a tube valve that is actuatable to selectively provide access to the tube lumen.

18. A hemostatic device in accordance with claim 12, wherein at least one of the locator device and the injection tube further comprises an indicator that indicates a length of at least one of the locator device and the injection tube.

19. A hemostatic device in accordance with claim 4, wherein the injection tube includes a plurality of discharge ports extending through the second sidewall and spaced substantially evenly about a circumference of the injection tube.

20. A hemostatic device in accordance with claim 4, wherein the device valve is longitudinally slideable along the sidewall to selectively restrict access to the first lumen.

* * * * *